United States Patent
Pufahl

[19]

[11] Patent Number: 5,922,428
[45] Date of Patent: Jul. 13, 1999

[54] STERILIZABLE PACKAGE WITH IMPROVED SEAL

[75] Inventor: John J. Pufahl, Lloyd Harbor, N.Y.

[73] Assignee: Adchem Corporation, Westbury, N.Y.

[21] Appl. No.: 08/931,394

[22] Filed: Sep. 16, 1997

[51] Int. Cl.$^6$ .................................................. B32B 3/00
[52] U.S. Cl. .................. 428/42.1; 206/411; 428/40.1; 428/41.9; 428/200; 428/202; 428/347; 428/352; 428/906
[58] Field of Search .................. 428/40.1, 41.9, 428/200, 202, 347, 354, 906, 42.1; 206/411

[56] References Cited

U.S. PATENT DOCUMENTS

| | | | |
|---|---|---|---|
| 2,954,915 | 10/1960 | Poepper | 229/66 |
| 2,997,166 | 8/1961 | Pratt | 206/56 |
| 2,998,880 | 9/1961 | Ladd | 206/63.2 |
| 3,057,471 | 10/1962 | Stonehill et al. | 206/63.3 |
| 3,217,871 | 11/1965 | Lee | 206/63.2 |
| 3,419,136 | 12/1968 | Pratt | 206/63.2 |
| 3,454,210 | 7/1969 | Spiegel et al. | 229/123.1 |
| 3,460,742 | 8/1969 | Langdon | 229/62 |
| 3,768,725 | 10/1973 | Pilaro | 229/66 |
| 3,935,810 | 2/1976 | Milano | 99/467 |
| 3,991,881 | 11/1976 | Augurt | 206/439 |
| 4,121,714 | 10/1978 | Daly et al. | 206/363 |
| 4,125,665 | 11/1978 | Bemmels et al. | 428/357 |
| 4,125,985 | 11/1978 | Laske | 53/452 |
| 4,194,622 | 3/1980 | Lewis | 206/363 |
| 4,199,645 | 4/1980 | Schwarz | 428/339 |
| 4,206,844 | 6/1980 | Thukamoto et al. | 206/439 |
| 4,276,982 | 7/1981 | Sibrava et al. | 206/439 |
| 4,358,015 | 11/1982 | Hirsch | 206/436 |
| 4,402,453 | 9/1983 | Regenstein, Jr. | 229/62 |
| 4,407,874 | 10/1983 | Gehrke | 428/215 |
| 4,417,658 | 11/1983 | Gardner et al. | 206/439 |
| 4,468,811 | 8/1984 | Shaw et al. | 383/5 |
| 4,509,196 | 4/1985 | Sak et al. | 383/5 |
| 4,510,621 | 4/1985 | Sak et al. | 383/89 |
| 4,545,843 | 10/1985 | Bray | 156/322 |
| 4,584,201 | 4/1986 | Boston | 426/106 |
| 4,599,276 | 7/1986 | Martini | 428/520 |
| 4,858,780 | 8/1989 | Odaka et al. | 220/359 |
| 4,874,090 | 10/1989 | Dyke | 206/439 |
| 4,937,040 | 6/1990 | Holcomb | 383/5 |
| 5,089,320 | 2/1992 | Straus et al. | 428/216 |
| 5,225,162 | 7/1993 | Scoville | 422/56 |
| 5,348,400 | 9/1994 | Haiss et al. | 383/210 |
| 5,353,573 | 10/1994 | Durrant | 53/410 |
| 5,355,656 | 10/1994 | Perrett | 53/373.7 |
| 5,401,533 | 3/1995 | Borland | 427/208.2 |
| 5,415,724 | 5/1995 | Perrett | 156/583.2 |
| 5,419,638 | 5/1995 | Jamison | 383/100 |
| 5,429,626 | 7/1995 | Fenton | 604/339 |
| 5,459,978 | 10/1995 | Weiss et al. | 53/425 |
| 5,474,818 | 12/1995 | Ulrich et al. | 428/34.3 |
| 5,486,389 | 1/1996 | Gerber | 428/41.9 |
| 5,502,952 | 4/1996 | Wildmoser | 53/455 |
| 5,549,388 | 8/1996 | Wilkes | 383/84 |
| 5,561,964 | 10/1996 | McIntyre et al. | 53/75 |
| 5,590,777 | 1/1997 | Weiss et al. | 206/439 |
| 5,629,079 | 5/1997 | Battles et al. | 442/60 |

*Primary Examiner*—Nasser Ahmad
*Attorney, Agent, or Firm*—Dilworth & Barrese

[57] ABSTRACT

A sterilizable package for medical instruments includes bonded first and second sheets of microbe impervious material at least one of which is sufficiently porous to allow the passage of gas therethrough. The first sheet has a flap which is folded over to seal the opening of the pouch. An adhesive sealing tape is bonded to the flap. The sealing tape includes a carrier strip, a first adhesive layer formed from heat seal adhesive and disposed on one side of the carrier strip, and a second adhesive layer formed from pressure sensitive adhesive disposed on an opposite side of the carrier strip. The first adhesive layer forms a heat seal bond between the carrier strip and the first sheet. The sterilizable pouch is resistant to tunneling or rippling of the package material which sometimes occurs during the sterilization process.

9 Claims, 3 Drawing Sheets

STERILIZABLE PACKAGE WITH IMPROVED SEAL

BACKGROUND

1. Field of the Invention

The present invention relates to a sterilizable package, and more particularly to a sterilizable pouch for medical and dental instruments, the pouch having an improved seal for closing the pouch.

2. Background of the Art

Medical instruments and supplies used in hospitals, clinics, and private offices of physicians and dentists are transported and/or stored in sterile packaging. Ordinarily, the unsterile device is first inserted into a pouch or envelope. The pouch is then sealed and sterilized.

Two common methods of sterilization are steam sterilization and sterilization with ethylene oxide gas. Both types of sterilization are performed at temperatures above 200° F. and with vacuum cycling. In order to insure sterilization of the medical instrument in the interior of the sealed pouch, at least one side of the pouch is a sheet of porous material such as, for example, a sheet fabricated from spun bonded polyolefin fibers. Such a sheet has a pore size sufficient to allow small molecules (water, ethylene oxide) pass through while blocking the entry of larger entities such as viruses and bacteria. The sealed pouch with medical instruments is placed in a chamber and subjected to cyclic treatment of steam or ethylene oxide alternated with vacuum treatment to remove the sterilizing gasses from inside the pouch. During the vacuum treatment especially, the pouch puffs-up until enough gas has escaped from within the pouch to equalize the internal and external pressures. This puffing-up of the pouch produces severe stress on the bonded areas between the sheets which are joined together to form the pouch.

Some types of pouches completely enclose the medical instrument by means of heat sealing the two sheets that form the pouch. Heat sealing requires special machinery and is generally feasible for use only at the factory.

Disposable instruments are generally packaged and sterilized at the factory. On the other hand, reusable instruments, especially dental instruments, are often sterilized on location at the hospital, clinic, or office. Pouches for enclosing reusable instruments are usually heat sealed at the factory on three sides, but have an open end which is sealed manually with a flap having a pressure sensitive adhesive tape.

U.S. Pat. No. 4,358,015 to Hirsch discloses a sterilizable pouch with a foldover flap having a double coated pressure sensitive adhesive tape affixed thereto. A release liner is provided for easier handling, the release liner having sterilization indicator ink printed on one side. The release liner can be peeled off the tape and inserted into the pouch before the pouch is sealed by the user. One problem is that to accept printing the liner cannot have a non-stick coating on the side on which the ink is to be applied. That is, the printed side of the liner must be adherable. However, if such a tape were rolled for storage the exposed adhesive side would contact the adherable side of the liner, thereby rendering the roll unusable. Therefore, where printed liners are used the roll of tape usually includes a secondary liner with single or double sided non-stick coatings. For example, the secondary liner can be used to cover the exposed pressure sensitive adhesive side of the tape. When the tape is rolled the pressure sensitive adhesive does not contact the printed adherable side of the release liner. The secondary liner is removed by the pouch manufacture to attach the adhesive tape to the foldover flap of the pouch. The release liner with the sterilization indicator is removed by the user prior to sealing the pouch. However, it would be advantageous to eliminate the need for a secondary liner, which represents additional cost.

A further problem with some pouches sealed with pressure sensitive adhesive flaps is "tunneling." That is, after the sterilization has been completed, ripples are sometimes observed on the sealing flaps of the pouches. These ripples can provide potential pathways, i.e., tunnels, for air and microorganisms to access the interior of the pouch. Thus, while sterilization of the interior of the pouch can be assured by certain indicators, continued maintenance of sterile conditions within rippled pouches can be in question.

It would be advantageous to reduce tunneling in pouches having pressure sensitive seals, and thereby insure the integrity of the sealed, sterilized instrument.

SUMMARY

A sterilizable package for medical instruments is provided herein. The package comprises a first sheet of microbe-impervious material having an end portion defining a foldable flap bonded to a second sheet of microbe-impervious material to form an enclosure space having an opening at least partially defined by an edge of said second sheet. A sealing tape is affixed to the foldable flap of the first sheet, the sealing tape including a film carrier, a first adhesive layer formed from heat seal adhesive and disposed on one side of the film carrier, and a second adhesive layer formed from pressure sensitive adhesive disposed on an opposite side of the film carrier. The first adhesive layer forms a heat seal bond between the film carrier and the first sheet.

The pouch preferably further includes a release liner attached to the second adhesive layer and is removable therefrom. Although the release liner has a plain paper side which is adherable, it can be rolled up with the sealing tape such that the first adhesive layer is in direct contact with an adherable plain paper side.

The first sheet is preferably fabricated from a porous material such as spun bonded polyolefin fiber. The second sheet is preferably a transparent polyester film such as polyethylene terephthalate bonded to the first sheet by heat sealable adhesive.

The carrier strip is a preferably a polyester film such as polyethylene terephthalate and has a thickness ranging from about 0.25 mils to about 0.6 mils.

The heat seal adhesive of the first adhesive layer is optionally a modified polyolefin composition having an activation temperature of from about 225° F. to about 250° F. and has a thickness of from about 1.0 mils to about 1.5 mils.

The pressure sensitive adhesive of the second adhesive layer is optionally an acrylic copolymer composition having a thickness of from about 1.0 mils to about 2.0 mils.

BRIEF DESCRIPTION OF THE DRAWINGS

Various embodiments are described herein with reference to the drawings, wherein.

DETAILED DESCRIPTION OF PREFERRED EMBODIMENT(S)

Figure 1:
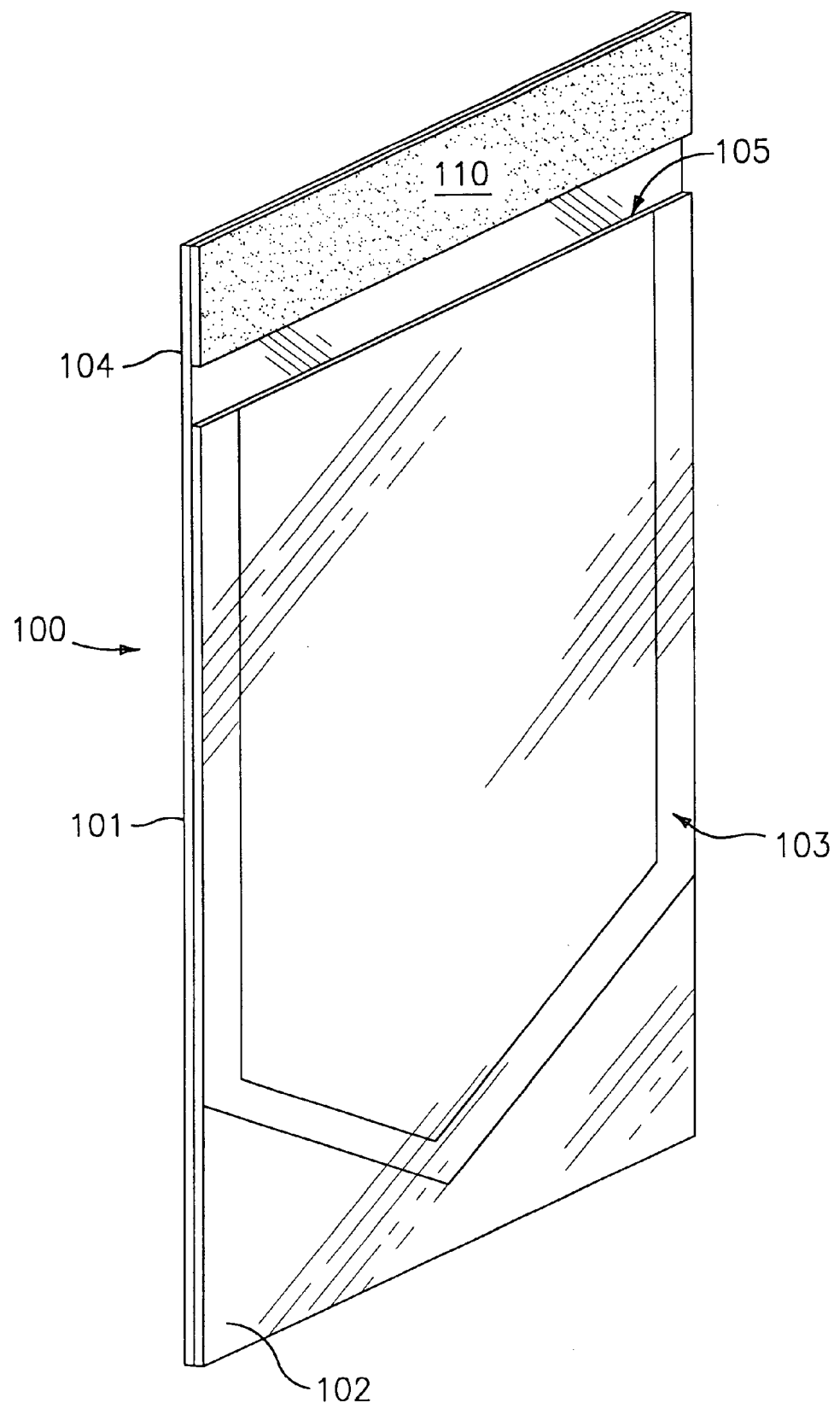
FIG. 1 is a perspective view of the pouch of the present invention.

Referring to FIG. 1, the package 100 of the present invention includes a first sheet 101 of microbe impervious material bonded to a second sheet 102 of microbe-impervious material by means of a peripheral seal 103.

First sheet 101 is preferably a sheet of spun bonded polyolefin fiber such as, for example, TYVEK® brand, and is sufficiently porous to permit the passage therethrough of gasses such as steam or ethylene oxide while providing a barrier against microorganisms. By way of example, first sheet 101 generally ranges in thickness from about 4 to about 6 mils (i.e., about 0.004 to about 0.006 inches). First sheet 101 has an extended portion forming a flap 104 which can be folded over to seal pouch 100, as described below.

Second sheet 102 is preferably non-porous and fabricated from a polyester such as polyethylene terephthalate film. Second sheet 102 can optionally have a polyolefin coating to facilitate heat sealing. By way of example second sheet 102 generally ranges in thickness from about 4 to about 6 mils. Second sheet 102 is preferably transparent to permit visualization of the contents of the package.

Seal 103 can be accomplished by any sealing method suitable for joining first and second sheets 101, 102 in a secure microbe-impervious bond which is capable of maintaining its strength and integrity under sterilization conditions. Seal 103 is preferably formed by any of the heat sealing methods known in the art which are appropriate for the purposes described herein. For example, an adhesive for heat sealing can be applied to one or the other of sheets 101 and 102, which may then be joined under heat and pressure. Alternatively, heat seal 103 can be formed by fusion bonding of the first and second sheets. As can be seen, edge 105 of the second sheet 102 is not sealed to the first sheet 101 in order to provide an opening for the insertion of medical instruments.

Figure 2:
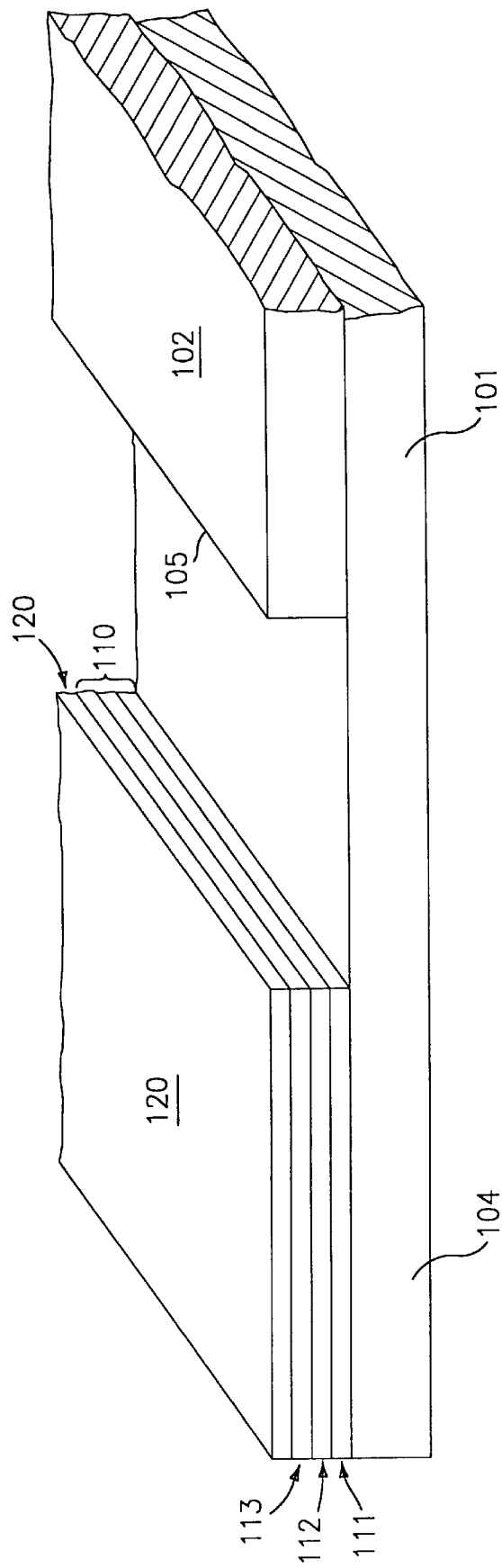
FIG. 2 is a partly sectional perspective view showing the foldable flap and adhesive tape.

Referring to FIG. 2, sealing tape 110 is bonded to flap 104 and provides adhesive means for sealing the pouch 100. Tape 110 comprises a first layer 111 of a heat seal adhesive, a middle carrier layer 112 of polymeric film, and a third layer 113 of pressure sensitive adhesive. It has been found that the heat seal adhesive bond between the tape 110 and the flap 104 greatly reduces tunneling.

More particularly, carrier layer 112 is preferably a backing material fabricated from a polyester such as polyethylene terephthalate. Alternatively, other polymeric materials such as polyethylene, polypropylene, and polyvinyl chloride films can also serve as carrier layers. By way of example, middle layer 112 preferably ranges from about 0.2 mils to about 1.0 mils in thickness, and more preferably from about 0.25 mils to about 0.6 mils in thickness.

The heat seal adhesive of first layer 111 is a thermoplastic polymer which is heated to render it of sufficient fluidity to facilitate application to a surface and which returns to a solid state when allowed to cool. Common heat seal adhesives are based on thermoplastic polymers such as polyolefins (e.g. polyethylene, polypropylene), ethylene-vinyl acetate copolymers, polyamides, polyesters, and block copolymer rubbers, for example. The flow characteristics and other properties of the thermoplastic polymer are typically modified by the addition of waxes, oils, terpene resins, and rosin derivatives, for example. The heat seal adhesive is applied in molten state to one side of carrier layer 112 and allowed to cool to a non-tacky condition. Generally, heat seal adhesives are not tacky unless heated to a certain minimum activation temperature of, for example, 225° F. to about 250° F. By way of example, first layer 111 preferably ranges in thickness from about 1.0 mils to about 1.5 mils, and more preferably from about 1.1 mils to about 1.3 mils. A heat seal adhesive useful for the purposes described herein is a modified polyolefin composition such as that available from E.I. DuPont de Nemours Co. under the designation ELVAX.

Pressure sensitive adhesives, such as that of third layer 113, are those which in dry form are tacky at room temperature. They adhere to a variety of different surfaces upon contact without the need of heat or of more than manually applied pressure. Pressure sensitive adhesives can be based on synthetic polymers such as styrene-diolefin triblock copolymers, polyisobutylene, styrene-butadiene, vinyl acetate copolymers, poly(vinylalkyl ether)s, and more preferably, alkyl acrylate polymers (acrylics) or 100% solids material that can be post cured with radiation (e.g., UV, electron beam). Tackifiers such as rosin esters, terpenes, copolymers of methylstyrene and vinyltoluene and the like, can be components of the pressure sensitive adhesive. The pressure sensitive adhesive of third layer 113 can be applied to the opposite side of carrier layer 112 by, for example, coating with a solution or emulsion of the pressure sensitive adhesive. By way of example, third layer 113 preferably ranges in thickness from about 1.0 mils to about 2.0 mils, and more preferably from about 1.4 mils to about 1.6 mils. A pressure sensitive adhesive suitable for use for the purposes described herein is an acrylic copolymer composition such as that available from Ashland Chemical Co. under the designation AROSET.

To facilitate handling of the sealing tape 110 a release liner 120 is applied to the pressure sensitive adhesive third layer 113. Release liner 120 is preferably fabricated from a paper stock as a support material, the paper having a non-stick coating on one side to prevent permanent bonding to the pressure sensitive adhesive. Silicone is the preferred non-stick coating material. Thus, release liner 120 is attached to second adhesive layer 113 but is easily removable therefrom by simply peeling it off.

Figure 4:
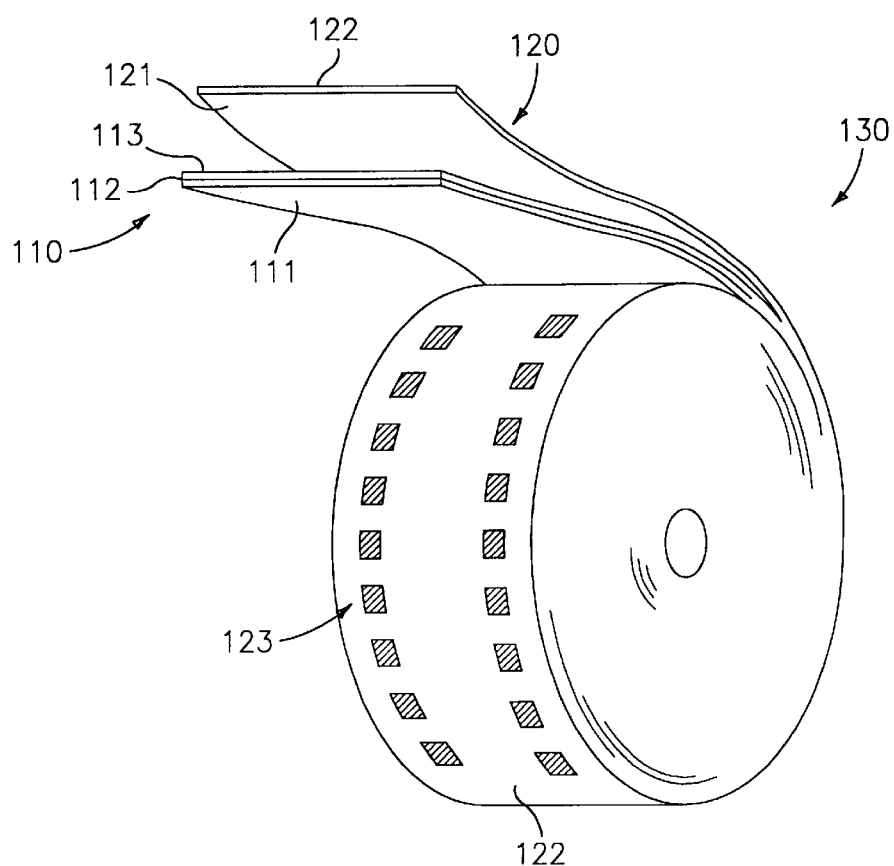
FIG. 4 is a perspective view of a roll of tape in accordance with the present invention.

Indicators can be used to determine whether the sterilization process has been effective. Such indicators can be associated with any portion of the pouch and typically are inks which change color upon exposure to the sterilizing agents and are described, for example, in U.S. Pat. Nos. 4,121,714, 4,194,622, 4,206,844, and 4,358,015, all of which are incorporated by reference. A significant advantage of the present invention is that the release liner 120 only needs to have a non-stick coating on one side. The other side can be plain paper capable of receiving an indicator ink. A secondary liner is not required. When the tape is rolled for storage the adhesive layer which contacts the adherable, plain paper side of the release liner 120 is the non-tacky heat seal adhesive of first layer 111. Referring to FIG. 4, a roll 130 of tape 110 and release liner 120 is shown. The release liner 120 has a non-stick side 121 coated with silicone (or other appropriate non-stick material) and an adherable, plain paper side 122 having printed indicia 123 which can be, for example, sterilization indicator ink. The adhesive tape 110 has a heat seal adhesive first layer 111, an intermediate carrier layer 112, and a pressure sensitive adhesive third layer 113. As can be seen, the heat seal adhesive first layer 111 at one portion of sealing tape 110 is in direct contact with the adherable side 122 of another portion of the release liner 120. No non-stick coating is applied to side 122, nor is another release liner required to contact heat seal adhesive layer 111.

Sealing tape 110, with release liner 120 applied to third layer 113, can be applied to portion 104 of first sheet 101 by means of heated rollers, or by preheating the tape 110 and first sheet 111 and then pressing them together.

Figure 3:
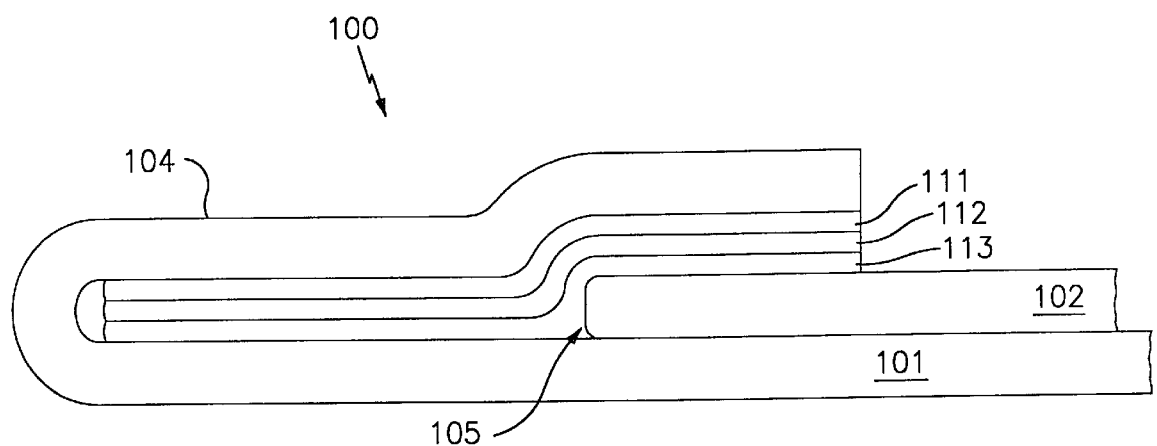
FIG. 3 is a side view showing the flap in folded over configuration for sealing the pouch.

To use package 100, the health care worker deposits the medical instrument in the interior of package 100, removes release liner 120 and then folds over flap 104 such that the pressure sensitive adhesive third layer 113 overlays the edge of second sheet 102 to seal the opening defined by edge 105. See, for example, FIG. 3, which shows the configuration of the folded flap 104. The release liner with printed sterilization indicator can be inserted into the package 100 before sealing to provide a visible indication of the completion of the sterilization.

The sealed package can then be sterilized by, for example, subjecting the package to steam or ethylene oxide. By way of example, steam sterilization is usually conducted at about 275° F. for about 45 minutes with alternating periods of steaming and application of vacuum. Ethylene oxide sterilization is typically conducted at about 250° F. for about 30–45 minutes with alternating periods of gassing and application of vacuum.

While the above description contains many specifics, these specifics should not be construed as limitations on the scope of the invention, but merely as exemplifications of preferred embodiments thereof. Those skilled in the art will envision many other embodiments within the scope and spirit of the claims appended hereto.

What is claimed is:

1. A sealing tape combination which comprises:
    a) a sealing tape having a carrier layer, a first adhesive layer formed from heat seal adhesive and disposed on one side of the carrier layer, and a second adhesive layer formed from pressure sensitive adhesive disposed on an opposite side of the carrier layer;
    b) a release liner fabricated from a support material having a first side coated with a non-stick material and an adherable second side, the first side being in contact with the second adhesive layer of the sealing tape, wherein the adherable second side of the release liner has indicia printed thereon, said indicia comprising sterilization indicator ink.

2. The sealing tape combination of claim 1 wherein the sealing tape combination is in a rolled configuration and the first adhesive layer of one portion of the sealing tape is in contact with the adherable second side of another portion of the liner.

3. The sealing tape combination of claim 1 wherein the support material of the release liner is paper.

4. The sealing tape combination of claim 1 wherein the non-stick material is a silicone.

5. The sealing tape combination of claim 1 wherein the heat seal adhesive is capable of withstanding steam sterilization.

6. The sealing tape combination of claim 1 wherein the heat seal adhesive is capable of withstanding ethylene oxide sterilization.

7. The sealing tape combination of claim 1 wherein the carrier layer has a thickness ranging from about 0.2 mils to about 1.0 mils.

8. The sealing tape combination of claim 1 wherein the first adhesive layer formed from heat seal adhesive has a thickness ranging from about 1.0 mils to about 1.5 mils.

9. The sealing tape combination of claim 1 wherein the second adhesive layer formed from pressure sensitive adhesive has a thickness ranging from about 1.0 mils to about 2.0 mils.

* * * * *